United States Patent

Takesako et al.

[11] Patent Number: 5,200,505
[45] Date of Patent: * Apr. 6, 1993

[54] R106 COMPOUNDS

[75] Inventors: Kazutoh Takesako, Kusatsu; Katsushige Ikai, Shiga; Kazuo Shimanaka, Tokyo; Junko Yamamoto, Moriyama; Fumiyo Haruna, Himeji; Teruya Nakamura, Kusatsu; Hideyo Yamaguchi, Kawasaki; Katsuhisa Uchida, Tokyo, all of Japan

[73] Assignee: Takara Shuzo Co., Ltd., Kyoto, Japan

[*] Notice: The portion of the term of this patent subsequent to Oct. 15, 2008 has been disclaimed.

[21] Appl. No.: 643,948

[22] Filed: Jan. 22, 1991

[30] Foreign Application Priority Data

Jan. 23, 1990 [JP] Japan .................................. 2-14384

[51] Int. Cl.$^5$ .............................................. C07K 11/02
[52] U.S. Cl. .................................... 530/323; 530/317
[58] Field of Search ................................ 530/317, 323

[56] References Cited

U.S. PATENT DOCUMENTS

| | | | |
|---|---|---|---|
| 4,342,751 | 8/1982 | Moore et al. | 514/9 |
| 4,737,487 | 4/1988 | Watts et al. | 514/15 |
| 5,057,493 | 10/1991 | Takesako et al. | 514/11 |

FOREIGN PATENT DOCUMENTS 0352092 1/1990 European Pat. Off. .

OTHER PUBLICATIONS

Cram et al., Organic Chemistry, 2nd Edition, McGraw-Hill Book Company pp. 607–613 (1964).

*Primary Examiner*—Y. Christina Chan
*Attorney, Agent, or Firm*—Wenderoth, Lind & Ponack

[57] ABSTRACT

There are provided R106 compounds represented by the following general formula (I):

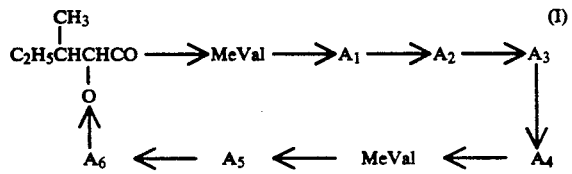

wherein:
$A_1$ is Phe, o-FPhe, m-FPhe, or Tyr;
$A_2$ is MePhe, o-FMePhe, m-FMePhe, MeTyr, Sar, MeSery, or β-oxoMePhe;
$A_3$ is Pro, 4Hyp, or SPro;
$A_4$ is allo-Ile or Nle;
$A_5$ is Leu or Nva;
$A_6$ is β-HOMeVal or Sar;

excluding those wherein $A_1$ is Phe and $A_2$ is MePhe and $A_3$ is Pro and $A_4$ is allo-Ile and $A_5$ is Leu and $A_6$ is β-HOMeVal (SEQ ID No. 4), which are useful as therapeutic agents for fungal infection.

1 Claim, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: circular ( v i ) ORIGINAL SOURCE:
        ( A ) ORGANISM: Aureobasidium ( i x ) FEATURE:
        ( A ) NAME/KEY: modified-site
        ( B ) LOCATION: 1
        ( C ) IDENTIFICATION METHOD:
        ( D ) OTHER INFORMATION: /note="MeVal"

( i x ) FEATURE:
        ( A ) NAME/KEY: modified-site
        ( B ) LOCATION: 3
        ( C ) IDENTIFICATION METHOD:
        ( D ) OTHER INFORMATION: /note=" N-methylphenylalanine, B-hydroxy-N- methylphenylalanine or Phe"

( i x ) FEATURE:
        ( A ) NAME/KEY: modified-site
        ( B ) LOCATION: 5
        ( C ) IDENTIFICATION METHOD:
        ( D ) OTHER INFORMATION: /note="aIle, Val or Leu"

( i x ) FEATURE:
        ( A ) NAME/KEY: modified-site
        ( B ) LOCATION: 6
        ( C ) IDENTIFICATION METHOD:
        ( D ) OTHER INFORMATION: /note="MeVal or Val"

( i x ) FEATURE:
        ( A ) NAME/KEY: modified-site
        ( B ) LOCATION: 8
        ( C ) IDENTIFICATION METHOD:
        ( D ) OTHER INFORMATION: /note="B-hydroxy-N-methylvaline, gamma-hydroxy-N-methylvaline, MeVal, Val, N,B-dimethylaspartic acid, B-hydroxy-N- methylphenylalanine, or N-methylphenylalanine."

( i x ) FEATURE:
        ( A ) NAME/KEY: modified-site
        ( B ) LOCATION: 8
        ( C ) IDENTIFICATION METHOD:
        ( D ) OTHER INFORMATION: /note="N-methyl-2,3-didehydrovaline or N-methyl-3,4-didehydrovaline."

( i x ) FEATURE:
        ( A ) NAME/KEY: modified-site
        ( B ) LOCATION: 8
        ( C ) IDENTIFICATION METHOD:
        ( D ) OTHER INFORMATION: /note="wherein the amino acid has a substituent 2-hydroxy-3-methylbutanoic acid or 2-hydroxy-3-methylpentanoic acid bound to location 1."

( x i ) SEQUENCE DESCRIPTION: SEQ ID NO:1:

Xaa Phe Xaa Pro Xaa Xaa Leu Xaa ( 2 ) INFORMATION FOR SEQ ID NO:2:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: circular ( v i ) ORIGINAL SOURCE:
        ( A ) ORGANISM: Aureobasidium ( i x ) FEATURE:
        ( A ) NAME/KEY: modified-site
        ( B ) LOCATION: 1
        ( C ) IDENTIFICATION METHOD:
        ( D ) OTHER INFORMATION: /note="MeVal"

( i x ) FEATURE:
        ( A ) NAME/KEY: modified-site
        ( B ) LOCATION: 2
        ( C ) IDENTIFICATION METHOD:
        ( D ) OTHER INFORMATION: /note="Phe, o-fluorophenylalanine, m-fluorophenylalanine, or Tyr"

( i x ) FEATURE:
        ( A ) NAME/KEY: modified-site
        ( B ) LOCATION: 3
        ( C ) IDENTIFICATION METHOD:
        ( D ) OTHER INFORMATION: /note=" N-methylphenylalanine, o-fluoro-N- methylphenylalanine, m-fluoro-N-methylphenylalanine, or N-methyltyrosine"

( i x ) FEATURE:
        ( A ) NAME/KEY: modified-site
        ( B ) LOCATION: 4
        ( C ) IDENTIFICATION METHOD:
        ( D ) OTHER INFORMATION: /note="Pro, 4Hyp, or thioproline"

( i x ) FEATURE:
        ( A ) NAME/KEY: modified-site
        ( B ) LOCATION: 5
        ( C ) IDENTIFICATION METHOD:
        ( D ) OTHER INFORMATION: /note="aIle or Nle"

( i x ) FEATURE:
        ( A ) NAME/KEY: modified-site
        ( B ) LOCATION: 6
        ( C ) IDENTIFICATION METHOD:
        ( D ) OTHER INFORMATION: /note="MeVal"

( i x ) FEATURE:
        ( A ) NAME/KEY: modified-site
        ( B ) LOCATION: 7
        ( C ) IDENTIFICATION METHOD:
        ( D ) OTHER INFORMATION: /note="Leu or Nva"

( i x ) FEATURE:
        ( A ) NAME/KEY: modified-site
        ( B ) LOCATION: 8
        ( C ) IDENTIFICATION METHOD:
        ( D ) OTHER INFORMATION: /note="B-hydroxy-N-methylvaline, wherein this amino acid has a substituent 2-hydroxy-3-methylpentanoic acid, which substituent is bound to the amino acid in location 1 to form the cyclic peptide."

( i x ) FEATURE:
        ( A ) NAME/KEY:
        ( B ) LOCATION:
        ( C ) IDENTIFICATION METHOD:
        ( D ) OTHER INFORMATION: /note="Excluding wherein position 2 is Phe, position 3 is N- methylphenylalanine, position 4 is Pro, position 5 is aIle and position 7 is Leu."

( x i ) SEQUENCE DESCRIPTION: SEQ ID NO:2:

Xaa Xaa Xaa Xaa Xaa Xaa Xaa Xaa
 1             5

(2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS: single
        (D) TOPOLOGY: circular (vi) ORIGINAL SOURCE:
        (A) ORGANISM: Aureobasidium (ix) FEATURE:
        (A) NAME/KEY: modified-site
        (B) LOCATION: 1
        (C) IDENTIFICATION METHOD:
        (D) OTHER INFORMATION: /note="MeVal"

(ix) FEATURE:
        (A) NAME/KEY: modified- site
        (B) LOCATION: 3
        (C) IDENTIFICATION METHOD:
        (D) OTHER INFORMATION: /note="N-methylphenylalanine, Sarcosine, N-methylserine or B-oxo-N-methylphenylalanine"

(ix) FEATURE:
        (A) NAME/KEY: modified-site
        (B) LOCATION: 5
        (C) IDENTIFICATION METHOD:
        (D) OTHER INFORMATION: /note="aIle"

(ix) FEATURE:
        (A) NAME/KEY: modified-site
        (B) LOCATION: 6
        (C) IDENTIFICATION METHOD:
        (D) OTHER INFORMATION: /note="MeVal"

(ix) FEATURE:
        (A) NAME/KEY: modified-site
        (B) LOCATION: 8
        (C) IDENTIFICATION METHOD:
        (D) OTHER INFORMATION: /note="B-hydroxy-N-methylvaline or Sarcosine, wherein the amino acid has a substituent 2-hydroxy-3-methylpentanoic acid which is bound to the amino acid in location 1 to form the cyclic peptide."

(ix) FEATURE:
        (A) NAME/KEY:
        (B) LOCATION:
        (C) IDENTIFICATION METHOD:
        (D) OTHER INFORMATION: /note="Excluding wherein location 3 is N-methylphenylalanine and location 8 is B-hydroxy-N-methylvaline."

(xi) SEQUENCE DESCRIPTION: SEQ ID NO:3:

Xaa Phe Xaa Pro Xaa Xaa Leu Xaa
1                    5

(2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS: single
        (D) TOPOLOGY: circular (vi) ORIGINAL SOURCE:
        (A) ORGANISM: Aureobasidium (ix) FEATURE:
        (A) NAME/KEY: modified-site
        (B) LOCATION: 1
        (C) IDENTIFICATION METHOD:
        (D) OTHER INFORMATION: /note="MeVal"

(ix) FEATURE:
        (A) NAME/KEY: modified-site
        (B) LOCATION: 2

(C) IDENTIFICATION METHOD:
(D) OTHER INFORMATION: /note="Phe, o-fluorophenylalanine, m-fluorophenylalanine, or Tyr"

(ix) FEATURE:
  (A) NAME/KEY: modified-site
  (B) LOCATION: 3
  (C) IDENTIFICATION METHOD:
  (D) OTHER INFORMATION: /note=" N-methylphenylalanine, o-fluoro-N- methylphenylalanine, m-fluoro-N-methylphenylalanine, N-methyltyrosine, Sarcosine, N-methylserine, or B-oxo-N-methylphenylalanine"

(ix) FEATURE:
  (A) NAME/KEY: modified-site
  (B) LOCATION: 4
  (C) IDENTIFICATION METHOD:
  (D) OTHER INFORMATION: /note="Pro, 4Hyp, or thioproline"

(ix) FEATURE:
  (A) NAME/KEY: modified-site
  (B) LOCATION: 5
  (C) IDENTIFICATION METHOD:
  (D) OTHER INFORMATION: /note="aIle or Nle"

(ix) FEATURE:
  (A) NAME/KEY: modified-site
  (B) LOCATION: 6
  (C) IDENTIFICATION METHOD:
  (D) OTHER INFORMATION: /note="MeVal"

(ix) FEATURE:
  (A) NAME/KEY: modified-site
  (B) LOCATION: 7
  (C) IDENTIFICATION METHOD:
  (D) OTHER INFORMATION: /note="Leu or Nva"

(ix) FEATURE:
  (A) NAME/KEY: modified-site
  (B) LOCATION: 8
  (C) IDENTIFICATION METHOD:
  (D) OTHER INFORMATION: /note="B-hydroxy-N-methylvaline or Sarcosine, wherein this amino acid has a substituent 2-hydroxy-3-methylpentanoic acid, which is bound to the amino acid in location 1 to form the cyclic peptide."

(ix) FEATURE:
  (A) NAME/KEY:
  (B) LOCATION:
  (C) IDENTIFICATION METHOD:
  (D) OTHER INFORMATION: /note="Excluding wherein location 2 is Phe, location 3 is N- methylphenylalanine, location 4 is Pro, location 5 is aIle, location 7 is Leu and location 8 is B-hydroxy-N-methylvaline"

(xi) SEQUENCE DESCRIPTION: SEQ ID NO:4:

Xaa Xaa Xaa Xaa Xaa Xaa Xaa Xaa
1               5

R106 COMPOUNDS

The present invention relates to novel R106 compounds which are useful as therapeutic agents for fungal infection.

As therapeutic agents for fungal infection, there are many known antibiotics including amphotericin B, flucytosine, miconazole, etc. However, these antibiotics are questionable in their activity and toxicity. In particular, there are only a few effective antifungal drugs for systemic fungal infections, which are recently increasing.

An object of the present invention is to provide novel drugs which have activity and low toxicity as therapeutic agents for fungal infection.

The present inventors searched for novel antibiotics and discovered antibiotics R106 represented by the following general formula (II) and identified in the attached Sequence Listing as SEQ ID No.1, which are produced by microorganisms belonging to Aureobasidium spp, including *Aureobasidium pullulans* No. R106 (FERM BP-1938) deposited at Fermentation Research Institute, Agency of Industrial Science and Technology, on Jul. 8, 1988. The invention of the antibiotics R106 is disclosed in U.S. Pat. No. 5,057,493.

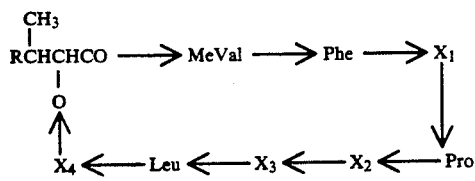

wherein:
R is methyl or ethyl;
$X_1$ is MePhe, $\beta$-HOMePhe or Phe;
$X_2$ is allo-Ile, Val or Leu;
$X_3$ is MeVal or Val;
$X_4$ is $\beta$-HOMeVal, $\gamma$-HOMeVal, MeVal, Val, N,$\beta$-MeAsp, $\beta$-HOMePhe, MePhe, MeDH$_{2,3}$Val or MeDH$_{3,4}$Val.

The present inventors furthermore searched for novel antifungal antibiotics in the fermentation broth of the antibiotics R106 producing organism described above and discovered novel R106 compounds represented by the following general formula (Ia) and identified in the attached Sequence Listing as SEQ ID No. 2:

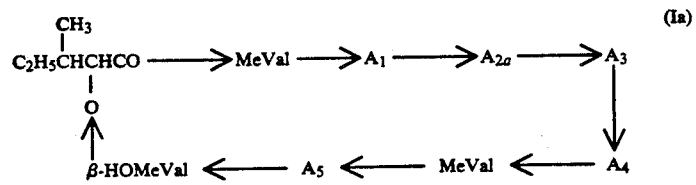

wherein:
$A_1$ is Phe, o-FPhe, m-FPhe, or Tyr;
$A_{2a}$ is MePhe, o-FMePhe, m-FMePhe, or MeTyr;
$A_3$ is Pro, 4Hyp, or SPro;
$A_4$ is allo-Ile or Nle;
$A_5$ is Leu or Nva;
excluding those wherein $A_1$ is Phe and $A_{2a}$ is MePhe and $A_3$ is Pro and $A_4$ is allo-Ile and $A_5$ is Leu.

And, the present inventors studied about the derivatives synthesized from R106-I (R; ethyl, $X_1$; MePhe, $X_2$; allo-Ile, $X_3$; MeVal, $X_4$; $\beta$-HOMeVal) or R106-IV (R, $X_2$, $X_3$, and $X_4$; same as those in R106-I, $X_1$; $\beta$-HOMePhe), which are included in the compounds represented by the general formula (II) indicated above, and have found novel R106 compounds represented by the following general formula (Ib) and identified in the attached Sequence Listing as SEQ ID No. 3.

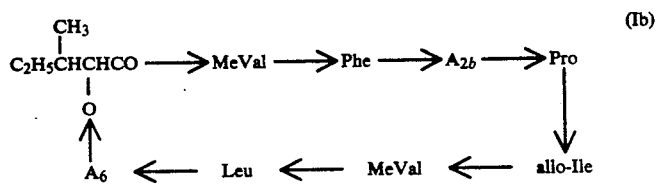

wherein:
$A_{2b}$ is MePhe, Sar, MeSer, or $\beta$-oxoMePhe,
$A_6$ is $\beta$-HOMeVal or Sar,
excluding those wherein $A_{2b}$ is MePhe and $A_6$ is $\beta$-HOMeVal.

As a result, the present invention has been completed by finding that the novel R106 compounds represented by the general formula (Ia) and (Ib) have strong antifungal activity and low toxicity.

Thus the present invention relate to novel R106 compounds represented by the general formula (I) and identified in the attached Sequence Listing as SEQ ID No. 4 described below:

$$\begin{array}{c}
\text{CH}_3 \\
| \\
\text{C}_2\text{H}_5\text{CHCHCO} \longrightarrow \text{MeVal} \longrightarrow A_1 \longrightarrow A_2 \longrightarrow A_3 \\
| \\
\text{O} \\
\uparrow \\
A_6 \longleftarrow A_5 \longleftarrow \text{MeVal} \longleftarrow A_4
\end{array} \quad (I)$$

wherein:
$A_1$ is Phe, o-FPhe, m-FPhe, or Tyr;
$A_2$ is MePhe, o-FMePhe, m-FMePhe, MeTyr, Sar, MeSer, or $\beta$-oxoMePhe;
$A_3$ is Pro, 4Hyp, or SPro;
$A_4$ is allo-Ile or Nle;
$A_5$ is Leu or Nva;
$A_6$ is $\beta$-HOMeVal or Sar;
excluding those wherein $A_1$ is Phe and $A_2$ is MePhe and $A_3$ is Pro and $A_4$ is allo-Ile and $A_5$ is Leu and $A_6$ is $\beta$-HOMeVal.

Novel R106 compounds of the present invention represented by the general formula (I) include the compounds shown in Table 1 as representative.

TABLE 1

$$\begin{array}{c}CH_3\\|\\C_2H_5CHCHCO\end{array} \longrightarrow MeVal \longrightarrow A_1 \longrightarrow A_2 \longrightarrow A_3 \quad (I)$$

$$A_6 \longleftarrow A_5 \longleftarrow MeVal \longleftarrow A_4$$

| Compound | $A_1$ | $A_2$ | $A_3$ | $A_4$ | $A_5$ | $A_6$ |
|---|---|---|---|---|---|---|
| 1 | o-FPhe | o-FMePhe | Pro | allo-Ile | Leu | β-HOMeVal |
| 2 | m-FPhe | m-FMePhe | " | " | " | " |
| 3 | Tyr | MeTyr | " | " | " | " |
| 4 | Phe | MePhe | 4Hyp | " | " | " |
| 5 | " | " | SPro | " | " | " |
| 6 | " | " | Pro | Nle | " | " |
| 7 | " | " | " | allo-Ile | Nva | " |
| 8 | Phe | Sar | " | " | Leu | β-HOMeVal |
| 9 | " | MeSer | " | " | " | β-HOMeVal |
| 10 | " | MePhe | " | " | " | Sar |
| 11 | " | Sar | " | " | " | Sar |
| 12 | " | β-oxoMePhe | " | " | " | β-HOMeVal |

Abbreviations for amino acids used in the present specification including the above formulas are given below.
Val: valine
MeVal: N-methylvaline
Nva: norvaline
β-HOMeVal: β-hydroxy-N-methylvaline
Phe: phenylalanine
MePhe: N-methylphenylalanine
β-HOMePhe: β-hydroxy-N-methylphenylalanine
β-oxoMePhe: β-oxo-N-methylphenylalanine
o-FPhe: o(ortho)-fluorophenylalanine
m-FPhe: m(meta)-fluorophenylalanine
o-FMePhe: o(ortho)-fluoro-N-methylphenylalanine
m-FMePhe: m(meta)-fluoro-N-methylphenylalanine
allo-Ile: alloisoleucine
Leu: leucine
Nle: norleucine
Pro: proline
4Hyp: 4-hydroxyproline
SPro: thioproline (thiazolidine-4-carboxylic acid)
MeSer: N-methylserine
Sar: sarcosine
Tyr: tyrosine
MeTyr: N-methyltyrosine Novel R106 compounds represented by the general formula (Ia) indicated above, which are included in the compounds represented by the general formula (I), may be produced by fermentation of an antibiotics R106-producing organism in a nutrient medium followed by purification. To the medium should be added one, two or more amino acids there are not components of antibiotics R106 represented by the general formula (II). These amino acids include o-fluorophenylalanine, m-fluorophenylalanine, tyrosine, 4-hydroxyproline, thioproline, norvaline, norleucine, etc. Microorganisms, which can be used for the production of novel R106 compounds of the present invention, can be a strain of the genus Aureobasidium which is capable of producing antibiotics R106. An example of the microorganisms is *Aureobasidium pullulans* No. R106 (FERM BP-1938), which can be used advantageously. The preferable amount of the amino acids to be added to the medium is usually 0.01~5.0% (w/v). Other ingredients to be added to the medium may be those that can be used for the production of antibiotics R106. The culture method may be that used for the production of antibiotics R106.

Novel R106 compounds accumulated in the cultured broth can be isolated by the procedures used for isolation of antibiotics R106. That is, novel R106 compounds can be purified by purification procedures, including extraction with a hydrophobic organic solvent such as ethyl acetate and chloroform, high performance liquid chromatography or column chromatography with silica-gel or octadecylsilanized (ODS) silica-gel etc.

Novel R106 compounds represented by the general formula (Ib) indicated above, which are included in the compounds represented by the general formula (I), may be produced from R106-I or R106-IV by a chemical modification described below.

For example, novel R106 compounds having sarcosine can be produced by converting β-hydroxy-N-methylvaline or β-hydroxy-N-methylphenylalanine contained in R106-I or R106-IV to sarcosine by retro-aldol reaction in the presence of a base catalyst. Usually, R106-I or R106-IV is dissolved in a hydrophilic solvent such as dimethylsulfoxide, acetonitrile and dimethylformamide, and to the solution is added a base catalyst to start reaction. As for the base catalyst, sodium hydroxide, potassium hydroxide, sodium hydride, or a tertiary amine such as triethylamine or the like can be used. For this reaction, the amount of water in the reaction system should be preferably reduced, because the ester bond in antibiotics R106 is hydrolyzed to by-produce a ring-opened compound when excess water is contained. The amount of the base, temperature and time for reaction may vary depending upon the base catalyst used, but generally 0.01-1.0%, 0° C. to a boiling point, and 10 minutes to a overnight, respectively.

When a quaternary ammonium salt, for example, tetraethylammonium chloride, β-(methoxyethoxymethyl)-triethylammonium chloride, etc. is used as a base catalyst, novel R106 compounds having N-methylserine is produced from R106-IV as a by-product by conversion of β-hydroxy-N-methylphenylalanine in R106-IV to N-methylserine besides to sarcosine.

Further, novel R106 compounds having β-oxo-N-methylphenylalanine as converted from β-hydroxy-N-methylphenylalanine in R106-IV can be produced by an oxidation reaction from R106-IV. General oxidation reagents, for example, chromic anhydride-sulfuric acid (Jones reagent), etc. and conventional oxidation methods may be used for the production of the object commands.

The representative compounds of the present invention have the following physicochemical and biological properties.

(1) Physicochemical properties

The representative compounds of the present invention shown in Table 1 have the physicochemical properties shown in Table 2.

Compounds 1, 2, 3, 4, 5, and 9 have higher solubility in water than antibiotics R106.

The minimum inhibitory concentrations (MIC, $\mu$g/ml) of the representative compounds of the present invention are shown in Table 3.

The MIC was determined by agar dilution method using Casitone agar medium (2.0% glucose, 0.9% Bacto-Casitone, 1.0% yeast extract, 0.1% $KH_2PO_4$, 0.1% $Na_2HPO_4$, 1.0% sodium citrate, 2.0% agar: concentrations are all by w/v).

Compound 8 is active against *Aspergillus fumigatus* F-48, against which antibiotics R106 are not active.

ii) Toxicity

When each of the representative compounds 1–12 of the present invention was administered intraperi-

TABLE 2

| Compound No. | Molecular Formula | Elementary analysis (%) | | | | | | FAB-MS | *Amino acid analysis |
|---|---|---|---|---|---|---|---|---|---|
| | | Found | | | Calcd. | | | | |
| | | C | H | N | C | H | N | | |
| 1 | $C_{60}H_{90}N_8O_{11}F_2$ | 63.01 | 8.16 | 9.41 | 63.36 | 7.98 | 9.85 | 1137 (M + H) 1159 (M + Na) | proline, alloisoleucine, leucine o-fluorophenylalanine |
| 2 | $C_{60}H_{90}N_8O_{11}F_2$ | 63.48 | 8.18 | 9.56 | 63.36 | 7.98 | 9.85 | 1137 (M + H) 1159 (M + Na) | proline, alloisoleucine, leucine, m-fluorophenylalanine |
| 3 | $C_{60}H_{92}N_8O_{13}$ | 63.24 | 8.41 | 9.37 | 63.58 | 8.18 | 9.89 | 1133 (M + H) 1155 (M + Na) | proline, alloisoleucine, leucine, tyrosine |
| 4 | $C_{60}H_{92}N_8O_{12}$ | 63.92 | 8.50 | 9.86 | 64.49 | 8.30 | 10.03 | 1117 (M + H) 1139 (M + Na) | 4-hydroxyproline, alloisoleucine, leucine, phenylalanine |
| 5 | $C_{59}H_{90}N_8O_{11}S$ | 62.91 | 8.26 | 9.63 | 63.30 | 8.04 | 10.00 | 1119 (M + H) 1141 (M + Na) | thioproline, alloisoleucine, leucine, phenylalanine |
| 6 | $C_{60}H_{92}N_8O_{11}$ | 65.13 | 8.72 | 9.75 | 65.43 | 8.42 | 10.17 | 1101 (M + H) 1123 (M + Na) | proline, leucine, norleucine, phenylalanine |
| 7 | $C_{59}H_{90}N_8O_{11}$ | 64.76 | 8.79 | 9.80 | 65.17 | 8.34 | 10.30 | 1087 (M + H) 1109 (M + Na) | proline, alloisoleucine, norvaline, phenylalanine |
| 8 | $C_{53}H_{86}N_8O_{11}$ | 62.30 | 8.81 | 10.38 | 62.95 | 8.57 | 11.08 | 1011 (M + H) 1033 (M + Na) | sarcosine, proline, alloisoleucine, leucine, phenylalanine |
| 9 | $C_{54}H_{88}N_8O_{12}$ | 61.84 | 8.73 | 10.29 | 62.29 | 8.52 | 10.76 | 1041 (M + H) 1063 (M + Na) | proline, alloisoleucine, leucine, phenylalanine |
| 10 | $C_{57}H_{86}N_8O_{10}$ | 65.11 | 8.18 | 10.53 | 65.62 | 8.31 | 10.74 | 1043 (M + H) 1065 (M + Na) | sarcosine, proline, alloisoleucine, leucine, phenylalanine |
| 11 | $C_{50}H_{80}N_8O_{10}$ | 63.10 | 8.63 | 11.33 | 63.00 | 8.46 | 11.75 | 953 (M + H) 975 (M + Na) | sarcosine, proline, alloisoleucine, leucine, phenylalanine |
| 12 | $C_{60}H_{90}N_8O_{12}$ | 64.19 | 8.30 | 9.81 | 64.61 | 8.13 | 10.05 | 1115 (M + H) 1137 (M + Na) | proline, alloisoleucine, leucine, phenylalanine |

*Detected by ninhydrin reaction using JCL-300 manufactured by JEOL Co., Ltd.

(2) Biological properties
i) Antifungal activity tioneally to mice once at a dose of 200 mg/kg, each compound caused no toxic sign.

TABLE 3

| Strain | MIC ($\mu$g/ml) Compound No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| *Candida albicans* TIMM 0136 | 0.10 | 0.20 | 0.10 | 0.05 | 0.05 | 0.20 | 0.05 | 0.10 | 6.25 | 25 | 25 | 0.10 |
| *Candida albicans* TIMM 0144 | 0.10 | 0.20 | 0.20 | 0.05 | 0.10 | 0.20 | 0.10 | 0.10 | 3.12 | 25 | 25 | 0.10 |
| *Candida albicans* TIMM 0171 | 0.10 | 0.10 | 0.10 | 0.05 | 0.05 | 0.20 | 0.10 | 0.05 | 1.56 | 3.12 | 6.25 | 0.10 |
| *Candida kefyr* TIMM 0301 | 0.20 | 0.78 | 0.39 | 0.20 | 0.20 | 1.56 | 0.20 | 0.10 | 3.12 | >25 | >25 | 0.39 |
| *Candida glabrata* TIMM 1062 | 0.20 | 0.78 | 0.78 | 0.20 | 0.39 | 0.78 | 0.20 | 0.78 | 12.5 | >25 | >25 | 0.20 |
| *Cryptococcus neoformans* TIMM 0354 | >25 | >25 | >25 | 3.12 | 6.25 | >25 | 6.25 | 12.5 | >25 | >25 | >25 | 12.5 |
| *Aspergillus fumigatus* F-48 | >25 | >25 | >25 | >25 | >25 | >25 | >25 | 12.5 | >25 | >25 | >25 | >25 |

Next, an example of the production method of R106-I and R106-IV, which are used as the starting materials for the production of the novel compounds of the present invention is shown below.

REFERENCE EXAMPLE

Production of R106-I and R106-IV

*Aureobasidium pullulans* No. R106 (FERM BP-1938) was inoculated into a 500 ml Erlenmeyer flask containing 100 ml of liquid medium (0.67% (w/v) Difco yeast nitrogen base, 2% glucose) and shaken at 25° C. for 2 days to give a seed culture. The seed culture, 1000 ml, was inoculated into a 200 liter jar fermenter containing 100 liter of liquid medium A (2% glucose, 0.5% $(NH_4)_2SO_4$, 0.15% $KH_2PO_4$, 0.05% $MgSO_4.7H_2O$, 0.01% $CaCl_2$, 0.01% NaCl (concentration are all by w/v), 0.5 µg/ml $FeCl_3$, 0.5 µg/ml $ZnSO_4$), followed by fermentation at 25° C. for 90 hours with aeration (100 liters/min) and agitation (150 rpm). To the culture was supplemented polypeptone (10 kg) dissolved in 10 liters of liquid medium B (ten-fold strength of liquid medium A), and the fermentation was further carried out at 25° C. for 90 hours with aeration (100 liters/min) and agitation (150 rpm).

The thus obtained fermentation broth was centrifuged to obtain mycelial cake, which was extracted with 10 liters of acetone. The acetone extract was concentrated under reduced pressure to remove acetone and the residue was extracted twice with one liter of ethyl acetate. The ethyl acetate extract was concentrated under reduced pressure to dryness, and the residue was dissolved in 100 ml of acetonitrile. The solution was divided into 30 and applied to preparative high performance liquid chromatography (HPLC) [column; SOKEN PAK $C_{18}$ (manufactured by Soken Chemical & Engeneering Co., Ltd.), 5×50 cm, mobile phase; 70% (v/v) acetonitrile-water, 50 ml/min, detection; UV absorption at 230 nm]. The fractions containing R106-IV and R106-I, eluted respectively at 50 min and 67 min of the retention time, were respectively collected and concentrated under reduced pressure of give white powders of R106-IV (81 mg) and R106I (3500 mg).

The present invention will be described in more detail by referring to the following examples. However, the present invention is not to be limited by these examples.

EXAMPLE 1

Preparation of compound No. 1

The seed culture, 1 ml, prepared in the same manner as in Reference example, was inoculated into a 500 ml Erlenmeyer flask containing 100 ml of the liquid medium A followed by shaking culture at 25° C. for 4 days to give a main culture A. To the main culture A was supplemented 10 ml of liquid medium B (ten-fold strength of liquid medium A) and 100 mg of o-fluorophenylalanine, and incubation was further carried out at 25° C. for 4 days.

The thus obtained culture broth (2.5 liters) was centrifuged to obtain mycelial cake, which was extracted with 250 ml of acetone. The acetone extract was concentrated under reduced pressure to remove acetone and the residue was extracted twice with 100 ml of ethyl acetate. The ethyl acetate extract was concentrated under reduced pressure to dryness, and the residue (1.5 g) was dissolved in methanol. The solution was divided into 40 and applied to preparative HPLC [column; YMC PAK $C_{18}$ (manufactured by YMC Co., Ltd.), 2×25 cm, mobile phase; 70% (v/v) acetonitrile-water, 10 ml/min, detection; UV absorption at 230 nm]. The fractions containing compound No. 1 were collected and concentrated under reduced pressure to give compound No. 1 (13 mg).

Molecular weight: FAB-MS m/z 1137 (M+H), 1159 (M+Na).

Amino acid analysis: proline, alloisoleucine, leucine, o-fluorophenylalanine.

EXAMPLE 2

Preparation of compound No. 2

To the main culture A, 100 ml, prepared in the same manner as in Example 1, was supplemented 10 ml of liquid medium B and 100 mg of m-fluorophenylalanine, and incubation under shaking was further carried out at 25° C. for 4 days.

The thus obtained culture broth (4.5 liters), was centrifuged to obtain mycelial cake. The mycelial cake was treated by the same purification procedures as in Example 1, including acetone extraction, ethyl acetate extraction, preparative HPLC, to give compound No. 2 (7 mg).

Molecular weight: FAB-MS m/z 1137 (M+H), 1159 (M+Na).

Amino acid analysis: proline, alloisoleucine, leucine, m-fluorophenylalanine.

EXAMPLE 3

Preparation of compound No. 3

To the main culture A, 100 ml, prepared in the same manner as in Example 1, was supplemented 10 ml of liquid medium B and 500 mg of L-tyrosine, and incubation under shaking was further carried out at 25° C. for 4 days.

The thus obtained culture broth (4.5 liters), was centrifuged to obtain mycelial cake. The mycelial cake was treated by the same purification procedures as in Example 1, including acetone extraction, ethyl acetate extraction, preparative HPLC, to give compound No. 3 (3 mg).

Molecular weight: FAB-MS m/z 1133 (M+H), 1155 (M+Na).

Amino acid analysis: proline, alloisoleucine, leucine, tyrosine.

EXAMPLE 4

Preparation of compound No. 4

To the main culture A, 100 ml, prepared in the same manner as in Example 1, was supplemented 10 ml of liquid medium B and 100 mg of L-4-hydroxyproline, and incubation under shaking was further carried out at 25° C. for 4 days.

The thus obtained culture broth (3.6 liters), was centrifuged to obtain mycelial cake. The mycelial cake was treated by the same purification procedures as in Example 1, including acetone extraction, ethyl acetate extraction, preparative HPLC, to give compound No. 4 (14 mg).

Molecular weight: FAB-MS m/z 1117 (M+H), 1139 (M+Na)

Amino acid analysis: 4-hydroxyproline, alloisoleucine, leucine, phenylalanine.

EXAMPLE 5

Preparation of compound No. 5

To the main culture A, 100 ml, prepared in the same manner as in Example 1, was supplemented 10 ml of liquid medium B and 500 mg of L-thioproline, and incubation under shaking was further carried out at 25° C. for 4 days.

The thus obtained culture broth (3.4 liters), was centrifuged to obtain mycelial cake. The mycelial cake was treated by the same purification procedures as in Example 1, including acetone extraction, ethyl acetate extraction, preparative HPLC, to give compound No. 5 (3 mg).

Molecular weight: FAB-MS m/z 1119 (M+H), 1141 (M+Na).

Amino acid analysis: thioproline, alloisoleucine, leucine, phenylalanine.

EXAMPLE 6

Preparation of compound No. 6

To the main culture A, 100 ml, prepared in the same manner as in Example 1, was supplemented 10 ml of liquid medium B and 100 mg of DL-norleucine, and incubation under shaking was further carried out at 25° C. for 4 days.

The thus obtained culture broth (2.1 liters), was centrifuged to obtain mycelial cake. The mycelial cake was treated by the same purification procedures as in Example 1, including acetone extraction, ethyl acetate extraction, preparative HPLC, to give compound No. 6 (48 mg).

Molecular weight: FAB-MS m/z 1101 (M+H), 1123 (M+Na).

Amino acid analysis: proline, leucine, norleucine, phenylalanine.

EXAMPLE 7

Preparation of compound No. 7

To the main culture A, 100 ml, prepared in the same manner as in Example 1, was supplemented 10 ml of liquid medium B and 100 mg of DL-norvaline, and incubation under shaking was further carried out at 25° C. for 4 days.

The thus obtained culture broth (2.7 liters), was centrifuged to obtain mycelial cake. The mycelial cake was treated by the same purification procedures as in Example 1, including acetone extraction, ethyl acetate extraction, preparative HPLC, to give compound No. 7 (12 mg).

Molecular weight: FAB-MS m/z 1087 (M+H), 1109 (M+Na).

Amino acid analysis: proline, alloisoleucine, norvaline, phenylalanine.

EXAMPLE 8

Preparation of compound Nos. 8 and 9

To a solution of R106-IV (99 mg) in anhydrous acetonitrile (20 ml) was added 40 mg of β-(methoxyethoxymethyl)triethylammonium chloride and the solution was refluxed for 16 hours. The reaction mixture was concentrated. To the residue was added water. The solution was extracted three times with ethyl acetate. The extract was concentrated under reduced pressure to dryness to give a residue (100 mg). The residue obtained was applied to preparative HPLC [column; CAPCELL PAK $C_{18}$ (manufactured by Shiseido), 1×25 cm, mobile phase; 70% (v/v) acetonitrile-water, 3 ml/min, detection; UV absorption at 230 nm] to collect separately fractions of compounds Nos. 8 and 9. The fractions are respectively concentrated under reduced pressure to dryness to give compound No. 8 (30 mg) and compound No. 9 (6 mg).

Compound No. 8

Molecular weight: FAB-MS m/z 1011 (M+H), 1033 (M+Na).

Amino acid analysis: sarcosine, proline, alloisoleucine, leucine, phenylalanine.

Specific rotary power: $[\alpha]_D^{20}-291.8$ (c 1.0, methanol)

Compound No. 9

Molecular weight: FAB-MS m/z 1041 (M+H), 1063 (M+Na).

Amino acid analysis: proline, alloisoleucine, leucine, phenylalanine.

Specific rotary power: $[\alpha]_D^{20}-235.3$ (c 1.0, methanol)

EXAMPLE 9

Preparation of compound No. 10

To a solution of R106-I (55 mg) in dimethylsulfoxide (5 ml) was added 8 μl of 6N aqueous NaOH, and the solution was stirred at room temperature for 25 min. The reaction mixture was concentrated to dryness under reduced pressure after neutralization with 1N aqueous HCl. The residue was extracted with ethyl acetate, and the extract was dryed and concentrated to dryness under reduced pressure to give a residue (56 mg). The residue was applied to preparative TLC [silica-gel plate of Merck No. 13895, solvent system: n-hexane-isopropanol (6:4)] and a fraction containing compound No. 10 was collected and eluted with 50 ml of chloroformmethanol (9:1). The eluate was concentrated to dryness under reduced pressure to give compound No. 10 (35 mg).

Molecular weight: FAB-MS m/z 1043 (M+H), 1065 (M+Na).

Amino acid analysis: sarcosine, proline, alloisoleucine, leucine, phenylalanine.

EXAMPLE 10

Preparation of compound No. 11

To a solution of R106-IV (56 mg) in dimethylsulfoxide (5 ml) was added 8 μl of 6N aqueous NaOH, and the solution was stirred at room temperature for 30 min. The reaction was then treated by the same procedures as in Example 9 to give compound No. 11 (28 mg).

Molecular weight: FAB-MS m/z 953 (M+H), 975 (M+Na).

Amino acid analysis: sarcosine, proline, alloisoleucine, leucine, phenylalanine.

EXAMPLE 11

Preparation of compound No. 12

In a solution of R106-IV (76 mg) in acetone (5 ml) was dropped 0.5 ml of Jones reagent. After 30 min stirring at room temperature, isopropanol (1 ml) was dropped in the solution under ice cooling. To the reaction solution was added water and extracted with ethyl acetate. The extract was concentrated to dryness under reduced pressure to give a residue (55 mg).

The residue obtained was applied to preparative HPLC [mobile phase; 80% acetonitrile-water, the other conditions were the same with those of Example 8] to collect fractions containing compound No. 12. The fractions were concentrated to dryness under reduced pressure to give compound No. 12 (20 mg).

Molecular weight: FAB-MS m/z 1115 (M+H), 1137 (M+Na).

Amino acid analysis: proline, alloisoleucine, leucine, phenylalanine.

The novel R106 compounds of the present invention have low toxicity and high antifungal activity against pathogenic fungi such as *Candida albicans* etc. Therefore the novel R106 compounds are useful as clinical drugs for fungal infections.

---

What is claimed is:
1. An R106 compound represented by the following formula (I):

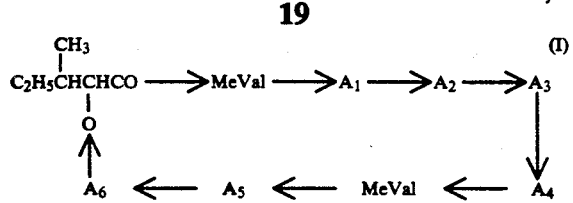
wherein:
A₁ is Phe, o-FPhe, m-FPhe, or Tyr;
A₂ is MePhe, o-FMePhe, m-FMePhe, MeTyr, Sar, MeSer, or β-oxoMePhe;
A₃ is Pro, 4Hyp, or SPro;
A₄ is allo-Ile or Nle;
A₅ is Leu or Nva;
A₆ is β-HOMeVal or Sar;
excluding those wherein A₁ is Phe and A₂ is MePhe and A₃ is Pro and A₄ is allo-Ile and A₅ is Leu and A₆ is β-HOMeVal (SEQ ID No. 4).
* * * * *